United States Patent [19]

Eiter

[11] 3,975,409

[45] Aug. 17, 1976

[54] PREPARATION OF CIS-7,8-EPOXY-2-METHYLOCTADECANE

[75] Inventor: Karl Eiter, Cologne, Germany

[73] Assignee: Bayer Aktiengesellschaft, Leverkusen, Germany

[22] Filed: Feb. 26, 1974

[21] Appl. No.: 446,064

Related U.S. Application Data

[63] Continuation of Ser. No. 284,826, Aug. 30, 1972, abandoned.

[30] Foreign Application Priority Data

Sept. 10, 1971 Germany............................ 2145454

[52] U.S. Cl. .................... 260/348.5 L; 260/345.9; 260/642 R; 260/678; 260/683 R; 260/348 R
[51] Int. Cl.² ................ C07D 301/12; C07C 11/22; C07C 5/16
[58] Field of Search .................. 260/348 R, 348.5 L

[56] References Cited
UNITED STATES PATENTS
3,453,362   7/1969   Cruickshank ....................... 260/348 R

OTHER PUBLICATIONS

B. A. Bierl et al., Science, vol. 170, Oct. 2, 1970, pp. 87–89.

B. B. Elsner et al., Jour. Chem. Soc. (London) (1953) pp. 3156–3160. 2-methyloctadecine-(7), hydrogenating

*Primary Examiner*—Norma S. Milestone
*Attorney, Agent, or Firm*—Burgess, Dinklage & Sprung

[57] ABSTRACT

The sexual attractant of the gypsy moth, cis-7,8-epoxy-2-methyloctadecane, is prepared by reacting isoheptyl bromide with an organometallic compound of dodecine-(1) in the presence of an anhydrous polar organic diluent at a temperature of about 20° to 150°C to produce 2-methyloctadecine-(7), hydrogenating the 2-methyloctadecine-(7) in the presence of a palladium catalyst and at a temperature of about −10° to +60°C in a diluent to produce 2-methyloctadecene-7-cis and epoxidizing the 2-methyloctadecene-7-cis to produce cis-7,8-epoxy-2-methyloctadecane. The organometallic compound of dodecine-1 is prepared by reaction of dodecine-1 with lithium, sodium or potassium amide freshly prepared in liquid ammonia or a solution of alkyl-lithium. The isoheptyl bromide is prepared by converting propargyl alcohol into 3-tetrahydropyranyloxypropine-(1), reacting the 3-tetrahydropyranyloxypropine-(1) with metallic lithium, sodium or potassium in liquid ammonia or with a Grignard compound to produce the corresponding organometallic compound, reacting the organometallic compound in an inert anhydrous organic solvent at a temperature of about −20° to +50°C with an approximately equimolar amount of freshly distilled isobutyraldehyde to produce 1-tetrahydropyranyloxy-5-methylhexin-(3)-ol-(4), hydrogenating the 1-tetrahydropyranyloxy-5-methylhexin-(3)-ol-(4) with excess Pd/carbon catalyst at a temperature of about 0° to 100°C to produce isoheptanol and converting the isoheptanol to isoheptyl bromide.

7 Claims, No Drawings

PREPARATION OF CIS-7,8-EPOXY-2-METHYLOCTADECANE

This is a continuation of applicaton Ser. No. 284,826, filed Aug. 30, 1972 and now abandoned.

The present invention relats to the stereospecific total synthesis of cis-7,8-epoxy-2-methyl-octadecane of the formula

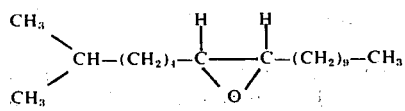

according to the building schemes $C_7 + C_{12} = C_{19}$

In 1960, M. Jacobson et al. [Science Washington 132, 1011 (1969); J. Amer. Chem. Soc. 83, 4819 (1961)] reported that the sexual attractant of the injurious insect *Porthetria dispar* (*Lymantria dispar*, gypsy moth, Schwammspinner) had been isolated and synthesized in the form of d,1-7-cis-10-acetoxyhexadecenol-(1). This substance could not be the true natural substance since a series of other authors have proved that this synthetic substance in the case of *Porthetria dispar* does not show the slightest biological activity [K. Eiter, E. Truscheit and M. Boness, Liebigs Ann. Chem. 709, 29-45 (1967), G. K. Stefanovic, B. Grujic-Inac, D. Micic, Zastita Bilja 73, 235 (1963)]. B. A. Bierl, M. Beroza and C. W. Collier (Science 170, 87, 1970) have since isolated the actual attractant from *Porthetria dispar* and recognized its constitution as cis-7,8-epoxy-2-methyloctadecane. Also described was a total synthesis of this compound which proceeded with a Wittig reaction according to the building schemes

but because of the laborious chromatographic adsorption which is necessary to separate the cis- and trans-olefins formed, this synthesis is not practical.

It has been found that the known cis-7,8-epoxy-2-methyloctadecane can be obtained in good yield by a surprising new process.

The invention provides a process for the production of cis-7,8-epoxy-2-methyloctadecane in which isoheptyl bromide is reacted with an organometallic compound of dodecine-(1) in the presence of an absolute polar organic solvent or diluent at a temperature of about 20° to 150°C to give 2-methyloctadecine-(7), the latter is hydrogenated sterospecifically in the presence of a palladium catalyst and at a temperature from −10° to +60°C in the presence of a solvent or diluent to give 2-methyloctadecane-7-cis, and the latter is opoxidized to give cis-7,8-epoxy-2-methyloctadecane.

Compared to the process described by B. A. Bierl, H. Beroza and C. W. Collier (Science 170, 87, 1970), the process according to he invention exhibits the great advantage of higher yield with simpler synthesis.

The isoheptyl bromide used in the process of the invention can be obtained in any convenient way. In particular it can be obtained in good yield by a novel method having the following steps.

Propargyl alcohol is converted in known manner into the tetrahydropyranyl ether and this 3-tetrahydropyranyloxypropine-(1) is converted into the organometallic compound either with metallic lithium, sodium or potassium in liquid ammonia or with methylmagnesium chloride, alkylmagnesium bromide or any other appropirate Grignard compound, in accordance with one of the following formula schemes:

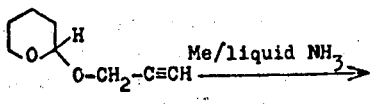

LeA 13914

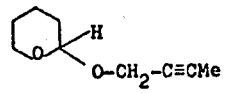

wherein:
Me is lithium, sodium or potassium, or

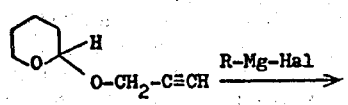

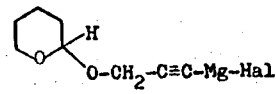

wherein
Hal is halogen, and
R is alkyl or other residue of a Grignard compound.

The so obtained organometallic compound of 3-tetrahydropyranyloxypropine-(1) can be reacted in any inert anhydrous organic solvent, such as ether, benzene, toluene, tetrahydrofuran or methylal, at about −20° to +50°C, preferably at about room temperature, with an equimolar amount of freshly distilled isobutyraldehyde to give 1-tetrahydropyranyloxy-5-methylhexin-(2) ol-(4). After decomposition of the reaction product with aqueous ammonium chloride solution, dilute cold acid or water alone, extraction may be effected with an organic solvent, such as ether, benzene or methylene chloride, followed by washing until the product is neutral; the extract is, optionally, dried, and the solvent is evaporated in a vacuum.

The 1-tetrahydropyranyloxy-5-methylhexin-(2)-ol-(4), may be hydrogenated with a little excess Pd/carbon catalyst at a temperature of about 0° to 100°C, preferably 20° to 50°C, to give the desired isoheptanol directly, perhaps in 50% yield. In this hydrogenation, a series of reaction steps take place simultaneously or successively, such as hydrogenation of the triple bond, dehydration and hydrogenation of the olefinic double bond formed, and splitting of the tetrahydropyran ring.

The isoheptanol so obtained may be brominated in known manner to give isoheptyl bromide.

Dodecine-(1) can be obtained, for example in 50% yield when a solution of 1-bromodecane in the same volume of an absolute polar solvent or diluent, preferably dimethyl formamide or dimethyl sulfoxide or diethyleneglycoldimethyl ether rendered anhydrous over $CaH_2$, is added dropwise at a temperature of about 50° to 100°C to a suspension of Bi-, Ma- or K-acetylide in a small amount of an absolute polar solvent or diluent, preferably in absolute tetrahydrofuran at 60°C; the conversion is exothermic. The reaction is allowed to continue afterwards for a further 1 to 2 hours at this temperature and the dodecine-(1) may then be worked up. If, both while preparing the relevant metal acetylide and while using dimethyl formamide, absolutely anhydrous conditions are not adhered to, there occurs, besides the formation of dodecine-(1), the formation to a greater or lesser extent of the ether

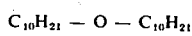

a compound crystallizing around 0°C which can be distilled as a colorless oil in a high vacuum.

The reaction of the organometallic compound of dodecine-(1) with isoheptyl bromide can be effected for example by any of the following methods:

a. Dodecine-(1) is reacted in liquid ammonia with lithium, sodium or potassium dissolved in the ammonia as an amide, to give the organometallic compound. The latter may be reacted, though in only relatively poor yields, in the same medium with isoheptyl bromide. Preferably 0.1 to 0.2 gram-atom of the alkali metal is dissolved in 200 to 300 ml of liquid ammonia at −35° to −40°C, the formation of the corresponding amide (after complete decolorizing) is awaited, and 0.1 to 0.2 mole of dodecine-(1) is then added dropwise. After a reaction period of 5 hours to 8 days, preferably 5 to 24 hours, 0.1 to 0.2 mole of isoheptyl bromide is added dropwise, again at −35° to −40°C, and reaction is allowed to take place at approximately −40°C for 5 hours to 8 days, preferably 5 to 24 hours, with stirring; the excess ammonia is carefully evaporated, the residue is optionally taken up with absolute tetrahydrofuran or dimethyl formamide or a mixture of these anhydrous solvents, and heating to 50° to 100°C is effected for several hours, preferably 3 to 5 hours. Decomposition can subsequently be effected with aqueous ammonium chloride solution.

Li-alkyl compounds may also be reacted with dodecine-(1) to form the organometallic compound. 2-methyloctadecine-(7) is able to be isolated in this way in 20% yield; both unreacted isoheptyl bromide and unchanged dodecine-(1) can be recovered by distillation.

b. In the case of the reaction of dodecine-(1) with for example methylmagnesium chloride or ethylmagnesium bromide in absolute ether, there is obtained, with formation of methane and of ethane, the organomagnesium compound of dodecine-(1) which, however, can be reacted with isoheptyl bromide in absolute THF under reflux conditions to give 2-methyloctadecine-(7) in traces only. On the other hand, with reaction in an autoclave at temperatures up to 150°C and reaction times of 5 to 10 hours, after working up, only up to a 10% yield of 2-methyloctadecine-(7) was obtained.

c. In the preferred method, 2-methyloctadecine-(7) is obtained in a yield of up to 60% or more. In this method, which is provided by the invention, the active metal amides are prepared in solution or as a very fine suspension in liquid ammonia in customary manner with lithium or sodium, or preferably potassium. An equimolar amount of dodecine-(1) is added dropwise at −35° to −40°C, and any excess ammonia is evaporated until the organometallic compound of the dodecine-(1) remains behind as residue. Absolute tetrahydrofuran is now added, preferably in a relatively small amount, heating to approximately 60°C is effected, and a solution of an equimolar amount of isoheptyl bromide in the same volume of anhydrous distilled dimethyl formamide is then added dropwise to this suspension.

With exothermic reaction there is formed 2-methyloctadecine-(7) of the formula

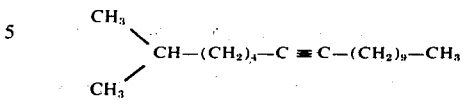

which may be obtained after working up with aqueous ammonium chloride solution and extraction with an organic solvent, after drying the solution and evaporating the solvent.

In the following step of the process of the invention, the triple bond of the 2-methyloctadecine-(7) can be hydrogenated stereospecifically, either with a modified "Lindlar" catalyst or, preferably with careful management of the reaction, directly with a 1% Pd/CaCO₃ catalyst, to give 2-methyloctadecene-7-cis of the formula

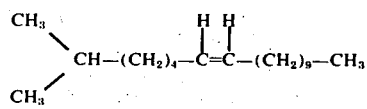

By modified Lindlar catalyst is meant a catalyst which is only so weakly poisoned with lead acetate that, for 5 g of a 15% Pd—CaCO₃ catalyst, only 20 mg of lead acetate are used for poisoning. For 0.02 mole of $C_{19}$-acetylene-hydrocarbon there are generally used 0.2 to 1.0 g of catalyst, preferably 0.5 to 1.0 g, and, as solvent, 50 to 100 ml of petroleum ether methanol, ethanol, tetrahydrofuran or dioxane. The hydrogenation proceeds under normal temperature and normal pressure; during hydrogen uptake, the temperature range should preferably be kept at about 20° to 25°C. Under these conditions, the hydrogenation ceases automatically after uptake of 1 mole of hydrogen, which can be observed from the falling off of the hydrogenation temperature.

When using pure 1% Pd—CaCO₃ catalyst, it is advisable to use, for 0.02 mole of $C_{19}$-acetylene-hydrocarbon, only 0.1 to 0.5 g of catalyst under the conditions stated above; it is surprising that with this catalyst, too, only a hydrogenation up to the cis-olefin stage is observed and the hydrogenation does not further proceed in uncontrolled manner, as would have been expected, up to the saturated $C_{19}$-hydrocarbon.

The hydrogenation may take place in a stirred hydrogenation apparatus intended for this purpose, in a shaking (duck-shaped) vessel or in a stirred autoclave. After filtration of the catalyst, the solvent may be evaporated in a vacuum and very pure 2-methyloctadecene-(7-cis) may be immediately obtained.

In the third step of the process of the invention, this olefin in epoxidized to give cis-7,8-epoxy-2-methyloctadecane, the natural attractant of the gypsy moth *Porthetria dispar* as mentioned above.

This epoxidation may be carried out by any convenient method. Various methods are known including the use of a per-acid, such as peracetic acid, perbenzoic acid, m-chloroperoxy-benzoic acid; in this case, epoxidation is advantageously effected with m-chloroperoxybenzoic acid. For this purpose, solutions of 2-methyloctadecene-7-cis in chloroform or methylene chloride may be used, and an equimolar solution of m-chloroperoxybenzoic acid in the same solvent added at −20° to +10°C, preferably approximately 0°C; reaction may be allowed to proceed to an adequate degree, for example for 12 hours at 0°C, with shaking; the separated m-chlorobenzoic acid is optionally filtered off, the organic phase being shaken until neutral with dilute alkali and water, drying effected, the solvent being evaporated; the compound can be obtained practically quantitatively in great purity.

The cis-7,8-epoxy-2-methyloctadecane obtained according to the invention represents the highly active sexual attractant of the forest pest *Porthetria dispar* which is indigenous for example to Europe. The synthetic attractant can, on account of its exceptional biological activity, be used in infested areas to attract the males of this injurious insect population. In contrast to the classic insecticides which are used in widespread fashion and strongly influence the environment, this compound can be used to attract the males to a single location where they can be destroyed, for example by a classic insecticide or in other manner. For this purpose, the attractant can be applied in highly dilute solutions in a solvent, for example benzene, hexane or petroleum ether; optionally, it can be applied after addition of antioxidants or stabilizers. Thus, in the control of injurious insects, with the increasing requirements of environment protection, there is provided an enormous technological advance, since the classic pesticides no longer have to be applied over wide areas with the known undesired side-effects (see K. Eiter, Insekten-Sexuallockstoffe in: R. Wegler, Chemie der Pflanzenschutz- und Schadlingsbekampfungsmittel Vol. 1, Springer-Verlag Berlin-Heidelberg-New York 1970, page 497).

The invention is further descirbed in the following illustrative examples wherein all parts are by weight unless otherwise expressed.

EXAMPLE I

Preparation of the isoheptanol serving as starting product:

A. Preparation of 1-tetrahydropyranyloxy-5-methyl-hexin-(2)ol-(4)

1. 0.2 g FeIII nitrate was added to 400 ml of liquid $NH_3$, and 7 g of Na metal are introduced at −30° to 40°C. At the same temperature, 35 g (0.25 M) of 3-tetrahydropyranyloxy-propine-(1) were added dropwise and the excess ammonia is slowly evaporated. At 0°C, 100 ml of absolute THF and 100 ml of absolute DMF were rapidly added to the residue, and into this suspension were introduced 40 g of freshly distilled isobutyraldehyde. Thawing to room temperature was effected, followed by stirring for 1 hour at this temperature; cooling to 0°C was effected, followed by careful decomposition with saturated $NH_4Cl$ solution. Extraction with ether was carried out, followed by washing; the ether phase was dried, evaporation was effected and the residue was distilled in an oil vacuum. b.p. at 0.15 mm Hg Fraction I 85°–125°C 15 g, $n_D^{20}$ 1.4620 carbinol
II 125–132°C 22 g, $n_D^{20}$ 1.4786 purest carbinol Fraction I + II = 37 g correspond to a 70% conversion. Redistillation yielded a product of $n_D^{20}$ 1.4791, which in the IR-, NMR-spectrum and elementary analysis corresponded completely to the desired 1-tetrahydroxypyranyloxy-5-methyl-hexin-(2)ol-(4).

$C_{12}H_{20}O_3$ (212.3) Calc. : C, 67.89; H, 9.50; O 22.61. Found : C, 67.8; H, 9.0; O, 22.7.

2. From 28.8 g of magnesium metal, 100 ml of absolute ether and 140 g of ethyl bromide in 240 ml of absolute ether a Grignard solution was prepared. When all had been reacted, 100 ml of absolute THF was run into the Grignard solution and, subsequently, a solution of 140 g of 3-tetrahydropyranyloxypropine-(1) in 200 ml of absolute THF was slowly added dropwise; when all had been introduced, heating to room temperature was slowly effected and, subsequently, heating to 30°C was effected for 1 hour; cooling to 0°C was then effected and a solution of 100 g of isobutyraldehyde in 200 ml of absolute ether was added dropwise; stirring at room temperature was effected for one hour and the contents of the flask were subsequently poured into a mixture of ice/sodium chloride, the solution was repeatedly extracted with ether, the ether extract was washed; drying and evaportion was effected. Crude yield 208 g; fractionation in an oil vacuum yields, at b.p. 0.1 mm Hg and 125°C, 144 g of 1-tetrahydroxypyranyloxy-5-methyl-hexin-(2)ol-(4) (68% of theory) of $n_D^{20}$ 1.4753.

3. Another preparative route proceeds via the alkylation of 3-tetrahydropyranyloxypropine-(1) with isobutyl bromide and hydrogenation of the so obtained 1-tetrahydropyranyloxy-5-methylhexine-(2).

1 g of FeIII nitrate was added at −35° to −40°C to 200 ml of liquid $NH_3$, and 7 g of metallic Na were gradually introduced in small pieces in such a manner that the blue coloring disappeared. After all the sodium had been reacted, 35 g of 3-tetrahydropyranyloxypropine-(1) were added dropwise, stirring at −35°C was effected for 2 hours and the excess $NH_3$ was slowly evaporated. At 0°C, 100 ml of absolute DMF was added to the solid resiude, and 40 g of isobutyl bromide were rapidly added dropwise at room temperature. Heating to 60°C was effected, the mixture was allowed to stand overnight at room temperature, and working up was effected with $NH_4Cl$ and ether in usual manner. 36.3 g of residue were obtained, the terminal acetylene group noted in the IR spectrum establishing the presence of unreacted starting material. By fractionation in an oil vacuum, at 0.15 mm Hg was distilled off below 65°C, and 5.3 g of the desired reaction product of $n_D^{20}$ 1.4626 distilled off at 65°–85°C according to the NMR spectrum the product consisted of the desired 1-tetrahydropyranyloxy-5-methyl-hexin-(2)ol-(4), and its gas chromatogram indicated a homogenity of 91%.

B. Preparation of isoheptanol.

1. 50 g of 1-tetrahydropyranyloxy-5-methylhexin-(2)ol-(4) were hydrogenated at 25°C in methanol with 2.5 g of 5% Pd carbon catalyst in a stirred autoclave. After filtration of the catalyst and distillation in an oil vacuum, three fractions were obtained, the middle fraction distilling off at 94°–98°C under 0.1 mm Hg, $n_D^{20}$ 1.4572.

Its gas chromatogram shows 76% homogeneity of 1-tetrahydropyranyloxy-5-methyl-hexanol-(4); in the IR spectrum, an impurity is found at 1710 $cm^{-1}$.

$C_{12}H_{24}O_3$ (216.3), Calc.: C, 66.63; H, 11.19; O, 22.18. Found: C, 67.7; H, 10.5; O, 21.7.

2. When the same hydrogenation was carried out in the presence of about 6 g of 5% Pd-carbon catalyst, in addition to 1-tetrahydropyranyloxy-5-methyl-hexanol-(4), isoheptanol was directly obtained in about 50% yield; b.p. 56°–90°C at 13 mm Hg, $n_D^{20}$ 1.4230–1.4260.

IR spectrum and refractive index, establish the product as isoheptanol.

3. Hydrogenation of 1-tetrahydropyranyloxy-5-methylhexine-(2) to give the tetrahydropyranyl ether of isoheptanol-5.3 g of 1-tetrahydropyranyloxy-5-methylhexine-(2) were dissolved in 100 ml of methanol in a shaking (duck-shaped) vessel, 0.2 g of 5% Pd/carbon catalyst were added, and hydrogenation was effected at 20°C until 2 moles of $H_2$ had been taken up. After filtration from the catalyst, the $CH_3OH$ was distilled off in a rotary evaporator and 5.4 g of residue were obtained whose IR spectrum, NMR spectrum and $n_D^{20}$ 1.4410 were identical to a known sample of 1-tetrahydropyranyl ether of isoheptanol. b.p. 0.1 mm Hg/70°–75°C.

EXAMPLE II

Preparation of dodecine-(1)

30 g (1.25 gram-atoms) of metallic sodium were pulverized at 100° to 110°C in 100 ml of absolute toluene. The toluene overlying the Na powder was, after cooling, carefully pipetted off, and the Na powder with 100 ml of absolute THF was transferred into a stirred apparatus filled with nitrogen. During heating to ~50°C, acetylene, which had been cooled and subsequently dried with concentrted $H_2SO_4$, was introduced at −70°C via a cold trap; after induction for some time, the formation of sodium acetylide set in as evidenced by generation of heat and yellow coloration. When after approximately 4 hours an exothermic reaction was no longer detectable, heating to 60°C was effected and, at this temperature, 170 g (0.8 mole) of 1-bromodecane dissolved in 100 ml of absolute DMF were added dropwise in such a manner that the temperature rose gradually to 70°C. The mixture was kept at this temperature for a further 2 hours, cooling being effected with carbonic acid-acetone; methanol, and then saturated ammonium chloride solution, were carefully added dropwise in order to decompose the excess sodium acetylide, extraction with ether was effected in customary manner, the ether extract was washed neutral with $NH_4Cl$ solution; drying was effected and the solvent was evaporated in a vacuum. There remained 150 g of residue which was fractionated in a water-jet vacuum. At 14 mm Hg the following fractions were collected at the indicated boiling points:

I  73–92°C  } dodecine-(1), yield 60 g
II 92–102°C

The fractions I and II were again rectified; dodecine-(1) distilled at 14 mm Hg from 90°–96°C. The IR spectrum of the substance showed the bands characteristic for terminal acetylene, the gas chromatogram showed it to be 90% pure and the NMR spectrum also showed the desired indications. $n_D^{20}$ 1.4342.

EXAMPLE II 2-methyloctadecine-(7)

A. 0.1 g of iron III nitrate was introduced into 200 ml of liquid $NH_3$, and 2.5 g of metallic sodium were dissolved in small pieces; after the contents of the flask had colored light-grey, 17.0 g dodecine-(1) were added dropwise; a white precipitate formed rapidly. Stirring at −35°C was effected for 6 hours, then 12 g of 1-bromo-5-methylhexane were added dropwise, further stirring was effected for 4 hours at −37°C and the mixture was left to stand overnight at −70°C. After the ammonia had been slowly evaporated off, 150 ml of absolute THF were added to the contents of the flask, heating to 70°C was effected for 3 hours; there were then added 20 ml of absolute DMF and distillation was effected with a descending condenser under normal pressure to remove the bulk of the THF. The remaining contents of the flask were cooled intensely, decomposed with aqueous ammonium chloride solution, extracted with ether several times, washed and dried. 20 g of an oil remained behind which was fractionated at 0.1 mm Hg. Fraction I  73–92°C  } dodecine-(1), yield 60 g
II 92–102°C The fractions I and II were chromatographed with petroleum ether on $Al_2O_3$ (Activity II) and eluted as a running fraction with petroleum ether. 5.1 g of $C_{19}$-acetyiene hydrocarbon b.p. 0.1 mm Hg 115° – 120°C air-bath temp., $n_D^{20}$ 1.4490. The gas chromatogram indicated the substance was, however, only 86% pure, while the mass spectrum showed, besides the mole peak 264, the strongest fragment at 123 ($C_9H_{15}$) which corresponds to a fragment piece beginning from the side of the isopropyl group of hydrocarbon molecule to the C atom of the 2-methylheptyne skeleton.

$C_{19}H_{36}$ (264.5) Calc.: C, 86.39; H, 13.61. Found: C, 85.4; H, 13.5.

MS Calc.: 264. MS Found: 264, 123, 99, 97, 85, 83, 71, 69, 57, 55, 43, 41.

B. Preparation of 2-methyloctadecine-(7) by brief reaction with sodium in liquid ammonia, addition of dodecine-(1) and isoheptyl bromide produced only traces of the desired $C_{19}$-acetylene hydrocarbon. Only a conversion of lithium in liquid ammonia over several days gave a good yield of the desired $C_{19}$-acetylene hydrocarbon.

1.4 g (0.2 gram-atom) of metallic lithium were dissolved in 200 ml of absolute liquid $NH_3$ at −30° to −40°C and stirred for several hours until the contents of the flask were completely decolorized. 34 g (0.2 mole) of dodecine-(1) were added dropwise to the white suspension and reaction was allowed to proceed (at −35°C by day, at −70°C by night) for 4 days. First 20.4 g of freshly distilled isoheptyl bromide, and after 8 days an additional 20 g of isoheptyl bromide, were added dropwise, and on the following day the agglomerated white mass was slowly freed of $NH_3$ by evaporation. The white viscous residue was taken up in 100 ml of absolute THF, heating to 70°C was effected for 5 hours, 5 ml of dimethyl formamide were added at intervals, and heating to the boil was effected for a further 2 hours. After evaporation in a rotary evaporator, the residue was able to be decomposed with ammonium chloride solution, extracted with ether with cooling, and the residue on evaporation was fractionated. Under 0.04 mm Hg at 135°–145°C there was obtained approximately 10 g of 2-methyloctadecine-(7), $n_D^{20}$ 1.4490 IR; NMR spectrum and GC were identical with the acetylene hydrocarbon described above.

C. 20 ml of a 13.8%-strength butyl-lithium/n-hexane solution were added to 7.0 g dodecine-(1) under purest nitrogen in 30 ml of diethyleneglycoldimethyl ether which had been rendered absolute over lithium alanate, and the n-hexane was distilled off on a descending condenser up to 100°C internal temperature. The temperature was allowed to rise to 120°C over 8 hours with stirring; 8.0 g of isoheptyl bromide were added dropwise at 120°C, rinsing was effected with a little diethyleneglycoldimethyl ether followed by heating, again with stirring, to 130°C for 8 hours. Working up yielded 7.8 g of 2-methyloctadecine-(7) (70% of theory) of b.p. 125°C at 0.4 mm Hg. IR, NMR spectra and elementary analysis were identical to the $C_{19}$-acetylene hydrocarbon obtained in the above experiments. $n_D^{20}$ 1.4500.

EXAMPLE IV

Preparation of 2-methyloctadecene-7-cis 5.28 g (0.02 mole) of 2-methyloctadecine-(7) were added to a prehydrogenated suspension of 1 g of catalyst in 50 ml of low-boiling petroleum ether (30°–50°C). The modified Lindlar catalyst was poisoned in such a manner that 0.02 g lead acetate was added, in the manner described in the literature, to 5 g of a 1% Pd catalyst precipitated on $CaCO_3$. At 765 mm Hg and an external temperature of 27.2°C, 0.02 mole $H_2$ = 490 ml. After a hydrogenation time of approximately 7 hours, 450 ml of $H_2$ had been taken up; the takeup of $H_2$ had come to a standstill after a further hour. Filtration from the catalyst was effected, the solvent was evaporated in a vacuum, and 5.7 g of 2-methyloctadecene-7-cis were obtained which is a bulb tube at 0.001 mm Hg came over at 110°–140°C air-bath temperature at a colorless oil, without residue $n_D^{20}$ 1.4471.

MS 266. MS found: 266, 15, 111, 97, 83, 69, 57, 55, 43.

According to its gas chromatogram, the substance was 95.4% pure. IR and NMR spectrum (60 + 220 MHz) prove the presence of the 7-cis configuration.

Analysis: $C_{19}H_{38}$ (266.5). Calc.: C, 85.63; H, 14.37. Found: C, 85.1; H, 14.7; C, 85.4; H, 14.4.

EXAMPLE V

Preparation of cis-7,8-epoxy-2-methyloctadecane 2.22 g of 2-methyloctadecene-7-cis were dissolved to 10 ml of absolute chloroform, and a solution of 1.6 g of m-chloroperoxybenzoic acid in 20 ml of absolute chloroform was added at 0°C. After a short period of shaking, m-chlorobenzoic acid precipitated in crystalline form; the mixture was allowed to stand overnight in a refrigerator; in the morning, filtration from the m-chlorobenzoic acid was effected, the chloroform solution was shaken neutral with 0.5 g of NaOH and water, drying was effected and the chloroform was evaporated off in a vacuum; 2.7 g of an oil remained behind which was distilled in a high vacuum in a bulb tube. After separation of a small preliminary portion at b.p. 0.01 mm Hg, 100°–110°C air-bath temp., $n_D^{20}$ 1.4462, a colorless thick oil came over at 110°–150°C air-bath temp., without residue.

Analysis: $C_{19}H_{38}O$ (282.5) Calc.: C, 80.78; H, 13.55; O, 5.67. Found: C, 80.7; H, 13.9; O, 5.8; C, 80.7; H, 13.9; O, 5.9.

It will be appreciated that the instant specification and examples are set forth by way of illustration and not limitation, and that various modifications and changes may be made without departing from the spirit and scope of the present invention.

What is claimed is:

1. In the production of cis-7,8-epoxy-2-methyl-octadecane wherein 2-methyloctadecene-7-cis is prepared and then epoxized, the improvement which comprises preparing the 2-methyloctadecene-7-cis by contacting isoheptylbromide with an organometallic compound of dodecine-(1) in the presence of an anhydrous polar organic diluent at a temperature of about 20° to 150°C to produce 2-methyloctadecine-(7), and hydrogenating the 2-methyloctadecine-(7) in the presence of a palladium catalyst and at a temperature of about −10° to +60°C in a diluent.

2. The process of claim 1, in which the organometallic compound of dodecine-1 is prepared by reaction of dodecine-1 with lithium, sodium or potassium amide freshly prepared in liquid ammonia or a solution of alkyllithium in an inert solvent.

3. The process of claim 1, in which the preparation of the 2-methyl-octadecine-7 is carried out at about 20°–130°C.

4. The process of claim 1, in which the hydrogenation is carried out at about 20° to 30°C.

5. The process of claim 1, in which the hydrogenation is carried out in the presence of about 0.2 to 1 gram of a modified Lindlar catalyst per 0.02 mole of 2-methyloctadecine-(7).

6. The process of claim 1, in which the hydrogenation is carried out in the presence of about 0.1 to 0.5 gram of a 1% Pd/$CaCO_3$ catalyst per 0.02 mole of 2-methyloctadecine-(7).

7. The process of claim 1, in which the isoheptyl bromide is prepared by converting propargyl alcohol into 3-tetrahydropyranyloxypropine-(1), reacting the 3-tetrahydropyranyloxypropine-(1) with metallic lithium, sodium or potassium in liquid ammonia or with a Grignard compound to produce the corresponding organometallic compound, reacting the organometallic compound in an inert anhydrous organic solvent at a temperature of about −20° to +50°C with an approximately equimolar amount of freshly distilled isobutyraldehyde to produce 1-tetrahydropryanyloxy-5-methylhexin-(3)-ol-(4), hydrogenating the 1-tetrahydropyranyloxy-5-methylhexin-(3)-ol-(4) with excess Pd/carbon catalyst at a temperature of about 0° to 100°C to produce isoheptanol, and converting the isoheptanol to isoheptyl bromide.

* * * * *